United States Patent [19]
Davidson et al.

[11] Patent Number: 6,153,076
[45] Date of Patent: *Nov. 28, 2000

[54] EXTENDED LENGTH MICROCHANNELS FOR HIGH DENSITY HIGH THROUGHPUT ELECTROPHORESIS SYSTEMS

[75] Inventors: James C. Davidson; Joseph W. Balch, both of Livermore, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/005,499

[22] Filed: Jan. 12, 1998

[51] Int. Cl.[7] .................................................. G01N 27/26
[52] U.S. Cl. ............................................. 204/601; 422/99
[58] Field of Search .................................... 204/450, 451, 204/600, 601; 422/50, 99, 100

[56] References Cited

U.S. PATENT DOCUMENTS

| | | | |
|---|---|---|---|
| 4,891,120 | 1/1990 | Sethi et al. | 204/600 |
| 4,908,112 | 3/1990 | Pace | 210/198.2 |
| 5,194,133 | 3/1993 | Clark et al. | 204/608 |
| 5,250,263 | 10/1993 | Manz | 422/81 |
| 5,681,484 | 10/1997 | Zanzucchi et al. | 216/2 |

OTHER PUBLICATIONS

S.C. Jacobson et al., Effects Of Injection Schemes and Column Geometry On The Performance of Microchip Electrophoresis Devices, Analytical Chemistry, vol. 66, No. 7, Apr. 1, 1994, pp. 1107–1112.

S.C. Jacobsen et al., Open Channel Electrochromatography On A Microchip, Analytical vol. 66, No. 14, Jul. 15, 1994, pp. 2369–2373.

*Primary Examiner*—Jill Warden
*Assistant Examiner*—Alex Noguerola
*Attorney, Agent, or Firm*—L. E. Carnahan; Alan H. Thompson

[57] ABSTRACT

High throughput electrophoresis systems which provide extended well-to-read distances on smaller substrates, thus compacting the overall systems. The electrophoresis systems utilize a high density array of microchannels for electrophoresis analysis with extended read lengths. The microchannel geometry can be used individually or in conjunction to increase the effective length of a separation channel while minimally impacting the packing density of channels. One embodiment uses sinusoidal microchannels, while another embodiment uses plural microchannels interconnected by a via. The extended channel systems can be applied to virtually any type of channel confined chromatography.

13 Claims, 1 Drawing Sheet

EXTENDED LENGTH MICROCHANNELS FOR HIGH DENSITY HIGH THROUGHPUT ELECTROPHORESIS SYSTEMS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to electrophoresis systems, particularly to high throughput microchannel systems, and more particularly to extended length high throughput microchannel electrophoresis system on mini-substrates.

High throughput electrophoresis systems depend on high densities of analysis channels/lanes. Electrophoretic separations use electric fields (high voltages) to separate analytes based on differences in migration velocities through sieving media or free solution. System currently in use require long separation columns to achieve the desired resolution of analytes such as proteins and DNA for example. Typical sample well-to-read lengths for DNA sequencing are between 24–30 cm. This requires large glass plates on the order of 42 cm long or long pulled capillaries. There has been a long felt need in this field of technology for a way to provide the needed sample well-to-read lengths without the use of large substrates, such as large glass plates, for example.

The present invention satisfies the above-referenced need by providing extended well-to-read distances on small substrates, thus compacting the overall system. Structures using microchannels are provided which can be used independently to extend channel length, one using sinusoidal channel configurations and another using interconnected channels. These structures can also be combined to further extend the overall length of channels in comparison of the prior utilized straight channel on a comparably sized substrate.

SUMMARY OF THE INVENTION

It is an object of the invention to provide extended well-to-read electrophoresis microchannels on small substrates.

A further object of the invention is to provide extended length microchannels on mini-substrates.

A further object of the invention is to provide extended length microchannels for high density, high throughput electrophoresis systems on mini-substrates.

Another object of the invention is to provide a high density array of microchannels for electrophoresis analysis with extended read length.

Another object of the invention is to provide microchannel geometries which can be used individually or in conjunction to increase the effective length of a separation channel while minimally impacting the packing density of the channels.

Another object of the invention is to provide structures including high density extended length microchannels for electrophoretic separations formed on small substrates using sinusoidal configured microchannels or interconnected microchannels to provide the desired well-to-read distances.

Other objects and advantages of the present invention will become apparent from the following description and accompanying drawings. Basically, the invention involves extended length microchannels for high density, high throughput electrophoresis systems on mini-substrates. This invention will permit the manufacture of a high density array of microchannels for electrophoresis analysis with extended read length The extended length microchannels are of a geometry which allows for use individually or in conjunction to increase the effective length of a separation channel with minimal impact on packing density of channels. The invention provides extended well-to-read distances on smaller substrates thus compacting the overall system. Two types of microchannel configurations are utilized to extend the overall channel length in comparison to straight channels on a comparably sized substrate. One channel configuration involves a sinusoidal arrangement while the other configuration involves interconnected channels.

The extended length microchannels of the present invention may be effectively utilized for high throughput DNA fragment and sequence analysis or other chromatographic systems, and can be applied to virtually any type of channel confined chromatography where extended readlength is required.

BRIEF DESCRIPTION OF THE DRAWINGS

The accompanying drawings, which are incorporated into and form a part of the disclosure, illustrate embodiments of the invention, and together with the description, serve to explain the principles of the invention.

DETAILED DESCRIPTION OF THE INVENTION

The present invention involves extended length microchannels for high density, high throughput electrophoresis systems, wherein the microchannels are configured and/or combined to have an extended length compared to the length of straight channels on a comparably sized substrate. Thus, the length of the substrate for long separation columns can be significantly reduced thus enabling compaction of the overall system. The extended length microchannels are formed on a substrate in either a sinusoidal configuration or an adjacent interconnected configuration The microchannel geometries can be used individually or in conjunction to increase the effective length of a separation channel while minimally impacting the packing density of channels.

Figure 1:
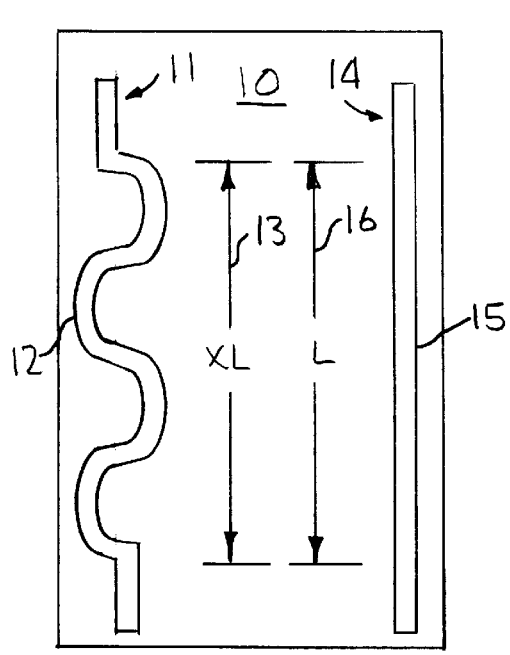
FIG. 1 illustrates a sinusoidal vs. straight line capillary arrangement which permits an arbitrary increase in length when located on a comparably sized substrate.
Figure 2:
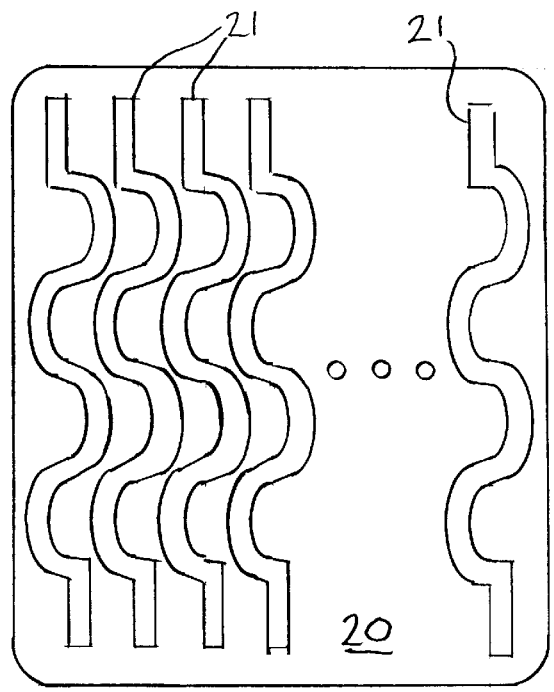
FIG. 2 illustrates an embodiment of a high density sinusoidal array of extended length microchannel capillaries.
Figure 3:
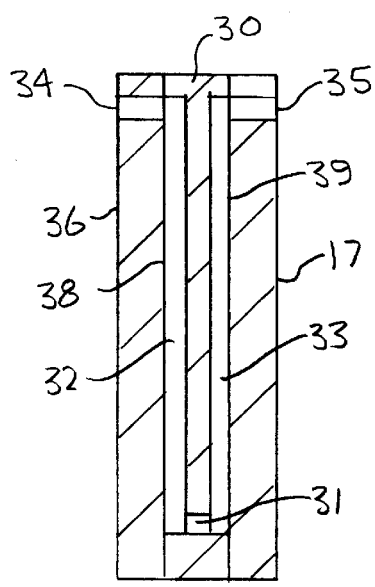
FIG. 3 illustrates a cross-sectional view of an embodiment of an extended length microchannel with channels and via on the same substrate.
Figure 4:
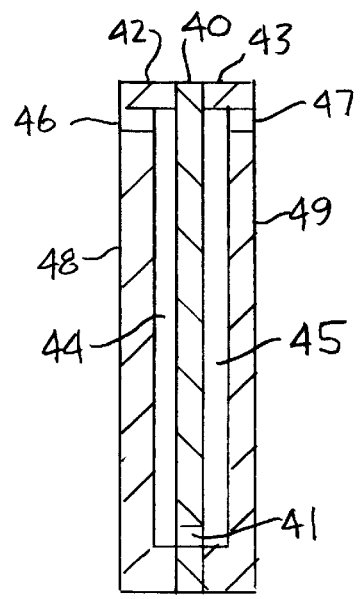
FIG. 4 illustrates a cross-sectional view of an embodiment of an extended length microchannel with channels and via on separate bonded substrates.

FIGS. 1–4 illustrate structures which incorporate the invention with FIG. 1 illustrating the extended channel length using a sinusoidal configuration compared to a straight configuration, while FIG. 2 illustrates an embodiment of a high density array of sinusoidal microchannels. FIG. 3 illustrates the extended channel length using two interconnected straight microchannels on the same substrate, while FIG. 4 illustrates the two interconnected adjacent straight microchannels on bonded separate substrates.

The structures illustrated in FIGS. 1 and 2 take advantage of increasing the overall length of an etched microchannel by sinusoidal undulations. Arbitrary lengths can be achieved by tailoring the frequency and amplitude of the sinusoidal structure. Example calculations show that the effective length for a semicircular or sinusoidal channel will be increased by a factor of 1.57 regardless of the radius of curvature. Using a semiellipitical profile where the long axis is twice the short axis the effective length is increased by a factor of 2.5. The approach of this invention facilitates the use of conventional microelectronics fabrication hardware to produce usable capillaries on small substrates. Arbitrary length channels can be etched in a substrate, such as glass, silicon, plastic, etc., and a top substrate or cover plate can be bonded to the etched substrate to effect a sealed capillary array. An additional feature of a sinusoidal type of channel is that the overall path length on either side of the center of the channel is the same. This provides consistency as opposed to coiled capillary approaches where the outer circumference is significantly greater than the inner circumference. Such a difference in pathlength due to curvature is reported to lead to a degration in resolution.

FIG. 1 illustrates a sinusoidal microchannel vs. a straight microchannel etched on a substrate, which permits an arbitrary increase in length. Here a substrate 10 includes a sinusoidal microchannel 11 having central section 12 of a length xL (x>b 1), as indicated by arrow 13; while a straight microchannel 14 has a similar central section 15 with a length of L as indicated by arrow 16. As exemplified above, the length xL may be a factor of 1.57, 2.5, etc. greater than length L depending on the configuration of the sinusoidal central section of the microchannels.

FIG. 2 illustrates an embodiment of a high density array of extended length sinusoidal microchannels. Here a substrate 20 is etched, for example, to form a plurality of sinusoidal microchannels 21, the number of microchannels 21 depending on the specific application as well as the width of the substrate 20 and the width of and separation distance between microchannels 21. For example, the substrate 20 may be constructed for electrophoresis of glass, plastic, selected ceramics, etc. having a length of 7 to 50 cm and a width of 2 to 15 cm; with the microchannels 21 having a depth of 10 to 200 $\mu$m, a length of 15 to 125 cm, width of 10 to 100 $\mu$m, and separation distance of 11 to 121 cm. Etching of the microchannels 21 in substrate 20 can be carried out using conventional techniques. While not shown, FIG. 2 would include a cover plate over the microchannels with the ends thereof connected to input and output as in FIGS. 3 and 4.

The structures illustrated in FIGS. 3 and 4 utilizes vias or holes etched or machined in a substrate with the microchannel etched on both sides of the substrate thereby doubling the effective channel length by joining channels on both sides of the substrate. Two approaches are illustrated which can produce the same overall structure. Both require two bonded interfaces to seal the channels. The first approach, as shown in FIG. 3, is accomplished by machining a via or hole in a substrate and then machining/etching a microchannel on both sides of the same substrate such that one end of the microchannels are in open communication with the via, and thereafter bonding a cover plate to the substrate on both sides so as to cover the microchannels. Two bonded interfaces are required. While not shown, the substrate could be provided with a number of spaced vias and a corresponding pair of microchannels for each via thereby producing a multi-channel electrophoresis system wherein each channel as in fact composed of two microchannels interconnected by a via whereby the overall length of the channel is about twice the length of the substrate. The second approach, as shown in FIG. 4, is to machine a via or hole in a thin "sandwich" substrate which is then bonded to substrates with microchannels etched/machined therein which are, and thereafter bonding cover plates on both sides to cover the microchannels. This approach also requires two bonded interface. The thickness of the via or sandwich substrate has to be great enough to withstand electrical breakdown. For example, a thickness of approximately 1 mm is required to withstand 10,000 volts, which is typical for electrophoresis systems.

FIG. 3 illustrates in cross-section the first approach described above, wherein a substrate 30 is provided with a via 31 and a pair of microchannels 32 and 33 which are at one end in communication with via 31 and at the other end in communication with an inlet 34 and an outlet 35, respectively, located in a pair of cover plates 36 and 37 bonded to substrate 30, with the bond interfaces indicated at 38 and 39. By way of example, the substrate 30 may be composed of glass, plastic, or ceramic having a thickness of 1 to 5 mm and length of 7 to 5 cm, with the via 31 having a diameter of 100 to 1000 $\mu$m; the microchannels 32 and 33 having a depth of 10 to 200 $\mu$m, width of 10 to 1000 $\mu$m, and length of 10 to 96 cm, with the cover plates 36 and 37 being constructed of glass, plastic, and ceramic, with a thickness of 1 to 5 mm; and with the interface bonds 38 and 39 being formed by thermal fusion or adhesive bonding.

The second approach is illustrated in cross-section in FIG. 4 wherein a sandwich substrate 40 containing a via 41 is bonded to substrates 42 and 43 containing microchannels 44 and 45 connected at the end to via 41 and at opposite ends to input 46 and output 47, respectively, in cover plates 48 and 49.

As pointed out above, each of the embodiments of FIGS. 3 and 4 may include multiple via/microchannel arrangements spaced along the width of the substrates so as to provide a multi-channel electrophores is system. The number of channels, and the perimeters of the microchannels and vias can be varied in accordance with different applications.

It has thus been shown that the present invention enables electrophoresis systems to utilize smaller substrates while having the needed well-to-read channel lengths, whereby the overall system may be more compact. Thus, mini-substrates may be provided with extended length microchannels to enable compact high density, high throughput electrophoresis systems.

While particular embodiments have been illustrated, it is within the scope of this invention to provide other extended length microchannel arrangements. For example, sinusoidal microchannels can be located on each side of the substrate and interconnected by vias, or to provide adjacent interconnected microchannels to extend the length of single straight microchannels.

While specific embodiments, parameters, materials, etc., have been illustrated and/or described to exemplify and teach the principles of the invention, such are not intended to be limiting. Modifications and changes may become apparent to those skilled in the art, and it is intended that the invention be limited only by the scope of the appended claims.

The invention claimed is:

1. In an electrophoresis system utilizing a substrate and a plurality of microchannels formed in parallel relationships in said substrate, the improvement comprising:

said microchannels are formed on opposite sides of the substrate and interconnected by a via; and each said microchannel having a sinusoidal configuration producing a length from a first point to a second point which is greater than a length of a straight microchannel extending from the first point to the second point and having an overall width on either side of a center of the microchannel which is the same, said sinusoidal configuration of each said microchannel being selected from the group consisting of semicircular arcs and semiellipitical profiles.

2. The improvement of claim 1, wherein each said sinusoidal configuration is selected from a group of configurations including a semicircular arc and a semiellipitical profile.

3. The improvement of claim 1, wherein each said sinusoidal configuration produces a microchannel length greater than a factor of 1 compared to a straight microchannel.

4. The electrophoresis system of claim 1, wherein, plurality of microchannels form an array of sinusoidal microchannels on at least one side of said substrate.

5. The improvement of claim 1, wherein said substrate is formed of bonded sections, and wherein said via is located in a different section of said substrate than said microchannels.

6. The improvement of claim 1, wherein said microchannels are formed in directly opposite sections of said sides of said substrate.

7. The improvement of claim 1, wherein said microchannels comprises a first section extending along a first surface of the substrate and a second section extending along a second surface face of the substrate;

said first and second microchannel sections being connected at one end to a via in said substrate.

8. The improvement of claim 7, wherein said first section of said microchannels is connected to an input, and said second section of microchannels is connected to an output.

9. The improvement of claim 7, additionally including cover plates over at least each of said first and second sections of said microchannels.

10. The improvement of claim 7, wherein said substrate is composed of sections bonded together, and wherein said via is located in a substrate section different from a substrate section containing the microchannel sections.

11. The improvement of claim 10, wherein said substrate is composed of three sections, and wherein said via is located in a middle substrate section.

12. The electrophoresis system of claim 1, wherein the improvement comprises a substrate with an array of said sinusoidal microchannels thereon, and wherein sections of each of said microchannels are located on different surfaces of said substrate and interconnected by a via in the substrate.

13. A compact electrophoresis system having a mini-substrate containing a number of microchannels each having a length from a first point to a second point greater than a length of a straight microchannel from the first point to the second point, each said microchannel being composed of at least two sections, said sections being interconnected by a via in the mini-substrate, each said microchannel having a sinusoidal configuration selected from the group consisting of a semicircular arc and a semiellipitical profile.

* * * * *